US008973197B2

United States Patent
Omidi

(10) Patent No.: US 8,973,197 B2
(45) Date of Patent: Mar. 10, 2015

(54) SANITIZING FLOOR MAT

(76) Inventor: Julian Omidi, Las Vegas, NV (US)

( * ) Notice: Subject to any disclaimer, the term of this patent is extended or adjusted under 35 U.S.C. 154(b) by 321 days.

(21) Appl. No.: 13/341,910

(22) Filed: Dec. 31, 2011

(65) Prior Publication Data

US 2012/0167325 A1    Jul. 5, 2012

Related U.S. Application Data

(60) Provisional application No. 61/428,980, filed on Dec. 31, 2010.

(51) Int. Cl.
*A47L 23/26* (2006.01)
*G08B 23/00* (2006.01)
*G01N 21/27* (2006.01)
*A61L 2/10* (2006.01)
*A61L 2/18* (2006.01)
*A61L 2/24* (2006.01)
*A61L 2/28* (2006.01)

(52) U.S. Cl.
CPC ............... *G01N 21/27* (2013.01); *G08B 23/00* (2013.01); *A47L 23/26* (2013.01); *A47L 23/263* (2013.01); *A61L 2/10* (2013.01); *A61L 2/18* (2013.01); *A61L 2/24* (2013.01); *A61L 2/28* (2013.01); *A61L 2202/17* (2013.01); *A61L 2202/20* (2013.01)

USPC .............................................. 15/36

(58) Field of Classification Search
CPC ................ A47L 23/26; G08B 23/00
USPC ................ 15/34, 36, 215, 216, 217
See application file for complete search history.

(56) References Cited

U.S. PATENT DOCUMENTS

| 345,291 | A | * | 7/1886 | Fein | 15/216 |
|---|---|---|---|---|---|
| 3,649,994 | A | * | 3/1972 | Harris | 15/311 |
| 4,425,677 | A | * | 1/1984 | Cox | 15/104.92 |
| 5,297,309 | A | * | 3/1994 | Rotoli | 15/104.92 |
| 5,991,967 | A | * | 11/1999 | Williams | 15/311 |
| 5,996,160 | A | * | 12/1999 | Pruitt | 15/104.92 |
| 6,886,210 | B2 | * | 5/2005 | Dean | 15/215 |
| 7,725,974 | B2 | * | 6/2010 | Hughes | 15/30 |
| 8,533,901 | B2 | * | 9/2013 | Williams | 15/311 |
| 2010/0193709 | A1 | * | 8/2010 | Dalton | 250/504 R |

* cited by examiner

*Primary Examiner* — Randall Chin
(74) *Attorney, Agent, or Firm* — David R Preston & Associates; James Fleming

(57) ABSTRACT

The present invention is comprised of an antibacterial door mat system for cleaning, disinfecting and detection of bacteria and other organisms on footwear to control spread of biological infections and contamination. The present invention is further comprised of an antibacterial door mat that cleans footwear, detects the presence of bacteria and a bio detection clearance door entry system that controls the entry into sterile areas.

6 Claims, 5 Drawing Sheets

SANITIZING FLOOR MAT

BACKGROUND

Life expectancy of humans has lengthened in part due to the awareness of microorganisms than cause infection and disease. This awareness has led to a progressive series of preventative measures to decrease the spread of microorganisms such as bacteria. Frequent hand washing, use of hand sanitizing lotions, wearing of gloves and other methods aid these measures. However the outside environment upon which people walk such as streets, sidewalks, grass and dirt are heavily contaminated with animal feces, litter, used nasal tissues and other forms of transmission of microorganisms. While clean hands and gloves help in keeping a setting such as a medical care area or a manufacturing clean room sterile the effort is some what futile if the contamination carried on footwear is allowed to enter the same area, unclean and unchecked for the presence of microorganisms such as bacteria.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized and structural changes may be made without departing from the scope of the present invention.

General Overview:

It should be noted that the descriptions that follow, for example, in terms of an antibacterial door mat system is described for illustrative purposes and the underlying system can apply to any number and multiple types of antibacterial door mat devices. In one embodiment of the present invention, the antibacterial door mat device may include optical chromatographic bio sensing systems. The antibacterial door mat system can be configured to include biochemical or other bio sensing systems and can be configured in a single platform or other forms, colors, shapes, sizes and depictions using the present invention.

Figure 1:
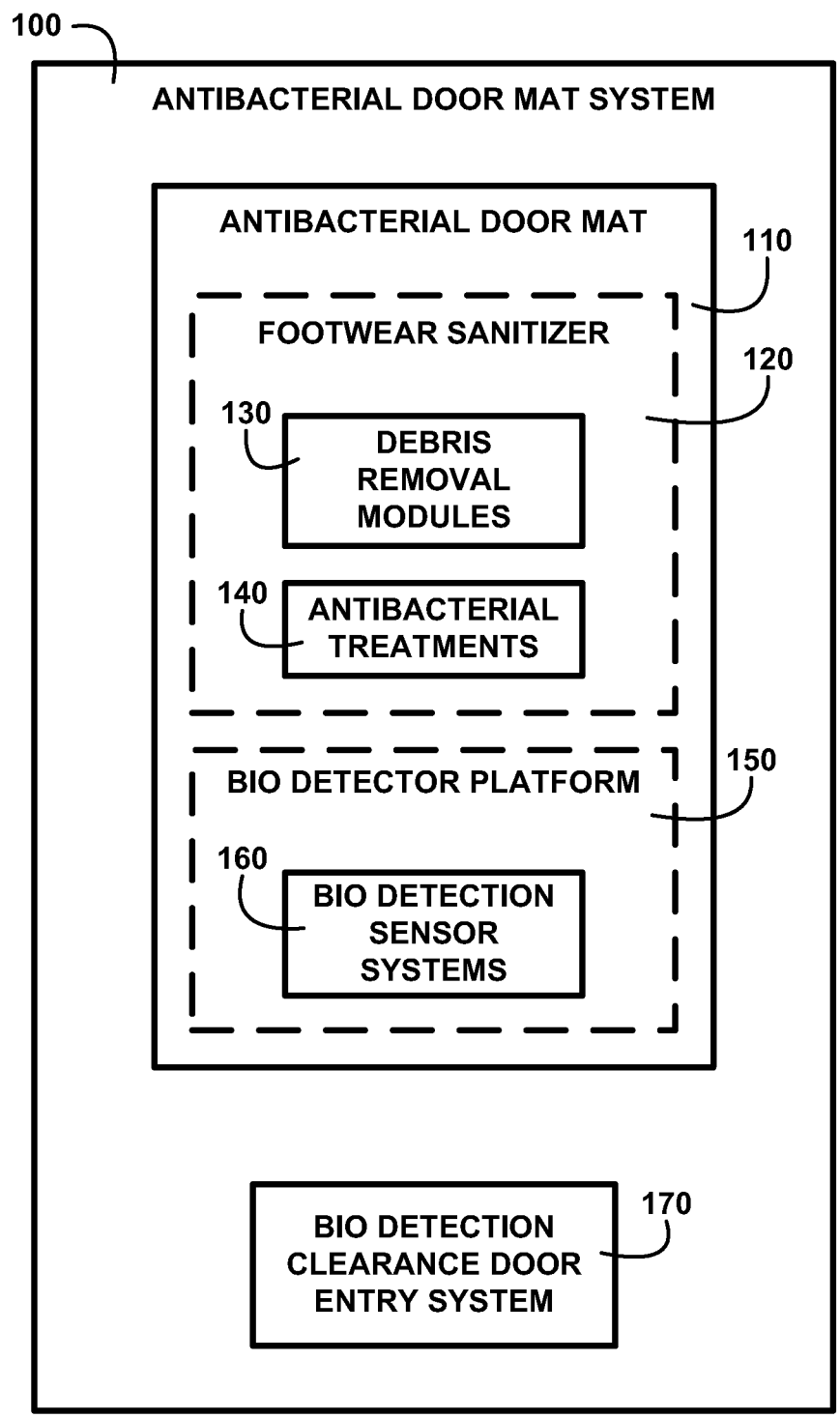
FIG. 1 shows a block diagram of an overview of an antibacterial door mat system of one embodiment of the present invention.

FIG. 1 shows a block diagram of an overview of an antibacterial door mat system of one embodiment of the present invention. FIG. 1 shows an antibacterial door mat system 100 for cleaning, disinfecting and detection of bacteria and other organisms on footwear to control spread of biological infections and contamination. The antibacterial door mat system 100 includes an antibacterial door mat 110 configured to clean and disinfect footwear and detect biological bacteria and other organisms.

The antibacterial door mat 110 includes a footwear sanitizer 120 and a bio detector platform 150. The footwear sanitizer 120 is configured to clean and disinfect footwear prior to biological detection inspection using the bio detector platform 150. The footwear sanitizer 120 is configured to allow a user to stand on the footwear sanitizer 120. The footwear of the user is cleaned of debris which may have adhered to the soles and sides of the footwear which the user walked on streets, sidewalks, grass or dirt which maybe contaminated. The soles and sides of the footwear are cleaned on the footwear sanitizer 120 by one or more debris removal modules 130. The debris removal modules 130 are configured to remove debris such as dirt, feces and other materials from the surfaces of the soles and lower portions of footwear. Following the cleaning cycle the footwear sanitizer 120 performs one or more antibacterial treatments 140 to the footwear. The antibacterial treatments 140 are configured to disinfect the surfaces of the soles and lower portions of footwear in preparation for biological detection inspection of one embodiment of the present invention.

The bio detector platform 150 is configured to expose the surfaces of the soles and lower portions of footwear to the operations of one or more bio detection sensor systems 160. The bio detection sensor systems 160 are configured to detect biological bacteria and other organisms on the surfaces of the soles and lower portions of footwear prior to entry into a sterile area. The bio detection sensor systems 160 can be configured to determine whether the cleaning operation removed bacteria and other microorganisms from the surfaces and display the results as a pass or fail clearance determination as a digital signal. The clearance digital signal is displayed on the bio detector platform 150 to notify the user of their status. If the clearance digital signal displays a fail indication the user can return to the footwear sanitizer 120 for an additional footwear cleaning cycle of one embodiment of the present invention.

The clearance digital signal can be configured to display on a monitor inside the area which the user desires to enter. The monitor displayed clearance status signal can be seen by appropriate personnel for example a security guard to open the entry door if a pass status is displayed. The bio detector platform 150 transmitted clearance digital signals can be configured to activate automatic opening of the area entry door using a bio detection clearance door entry system 170 component of the antibacterial door mat system 100. The bio detection clearance door entry system 170 receives the clearance digital signal and can for example activate unlocking of an electronic locking device configured into the entry door to open if the signal received indicates a pass. The antibacterial door mat system 100 can reduce and prevent the spread of footwear borne bacteria and other organisms which can pose infectious and potentially hazardous contamination of sterile environments of one embodiment of the present invention.

Detailed Operation:

The foregoing has described the principles, embodiments and modes of operation of the present invention. However, the invention should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

Figure 2A:
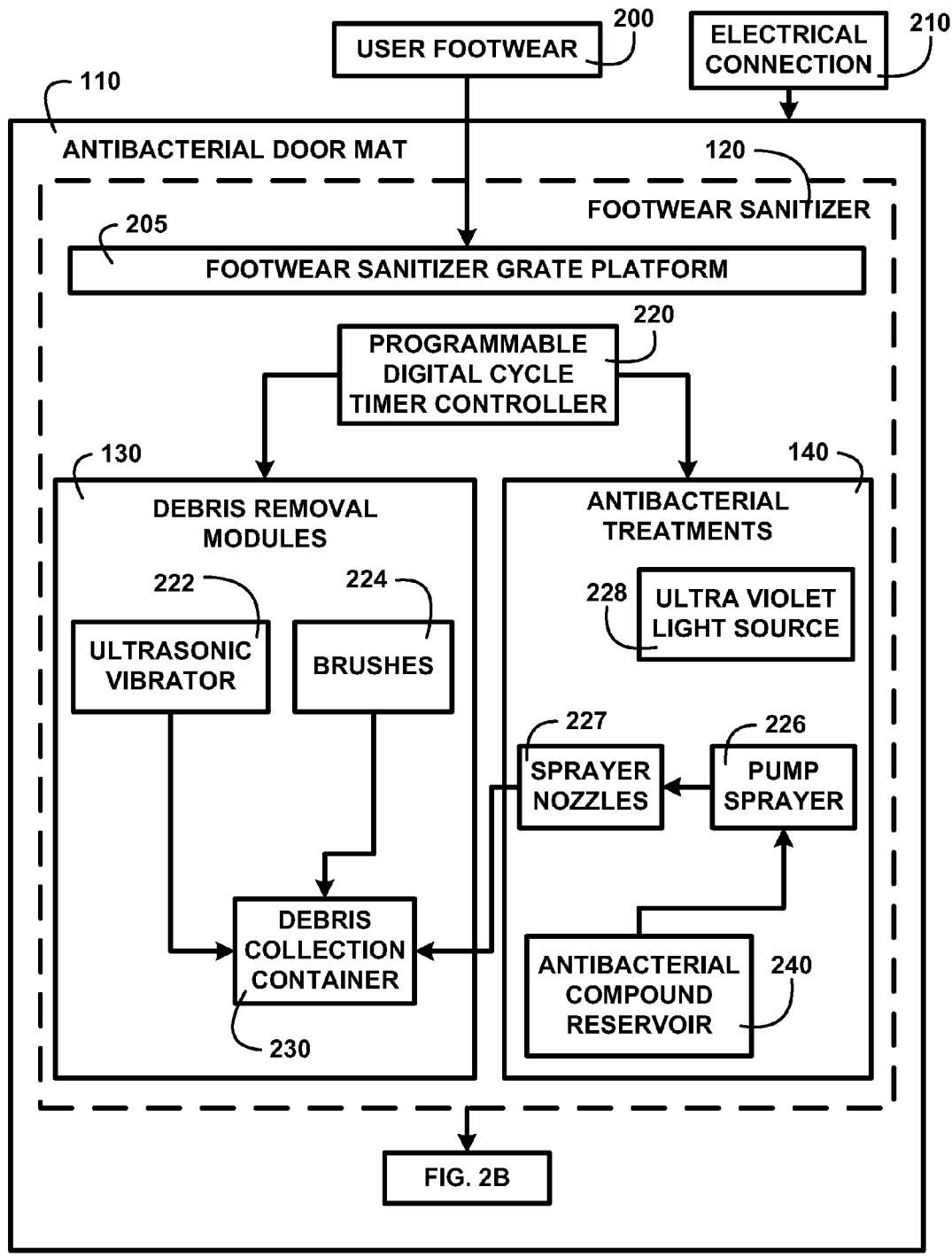
FIG. 2A shows a block diagram of an overview flow chart of an antibacterial door mat system footwear sanitizer system of one embodiment of the present invention.
Figure 2B:
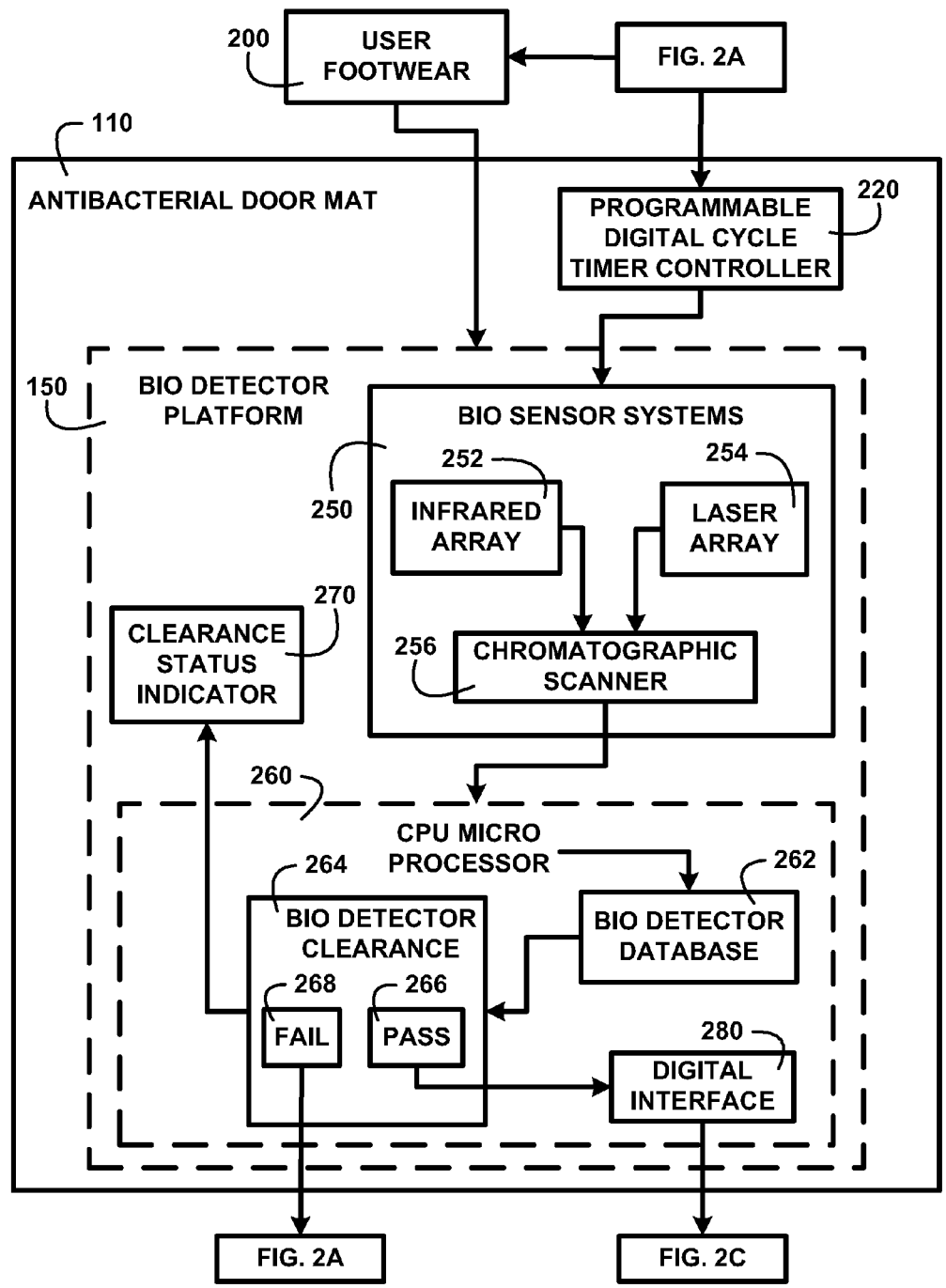
FIG. 2B shows a block diagram of an overview flow chart of an antibacterial door mat system bio detector platform system of one embodiment of the present invention.
Figure 2C:
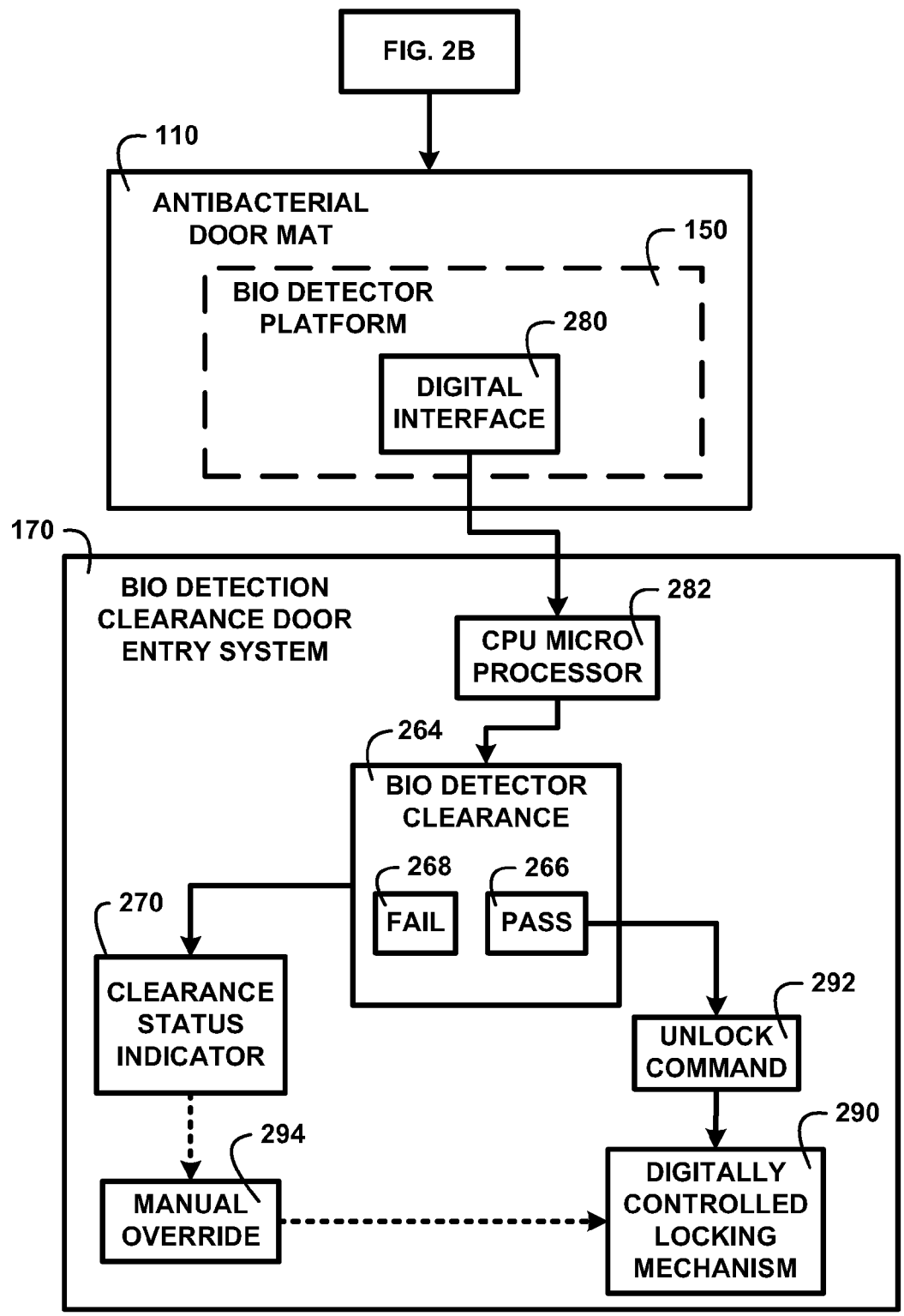
FIG. 2C shows a block diagram of an overview flow chart of an antibacterial door mat system bio detection clearance door entry system of one embodiment of the present invention.

The overview flow chart of the antibacterial door mat system 100 of FIG. 1 is shown in FIG. 2A, FIG. 2B and FIG. 2C of one embodiment of the present invention. The application of the antibacterial door mat system 100 of FIG. 1 can be configured to provide decontamination and biological sanitizing functions in medical facilities, dean room and other areas that are sensitive to prevention of infection, contamination and biological hazards of one embodiment of the present invention.

Footwear Sanitizer System:

FIG. 2A shows a block diagram of an overview flow chart of an antibacterial door mat system footwear sanitizer system of one embodiment of the present invention. FIG. 2A shows an electrical connection 210 used to power the operation of the antibacterial door mat 110 of the antibacterial door mat system 100 of FIG. 1. The electrical connection 210 can be configured as a battery pack of rechargeable batteries or a cabled electrical cord connected to an outlet. The antibacterial door mat 110 includes a programmable digital cycle timer controller 220 to regulate the sequence and period of time of the operation of processing elements of a footwear sanitizer using digital codes and instructions. The user stands on a footwear sanitizer grate platform 205 of the footwear sanitizer 120 in preparation of the cleaning and sanitizing of user footwear 200 of one embodiment of the present invention.

The footwear sanitizer grate platform 205 can be configured of various materials and designs for example rectangular metal bars spaced evenly and connected by metal rods or high density plastic rods molded as a cross hatched matrix. The footwear sanitizer grate platform 205 can be configured to attach to one or more ultrasonic vibrator 222. The ultrasonic vibrator 222 attached to a spring mounted footwear sanitizer grate platform 205 can be one form of the debris removal modules 130. The vibration at high rates for example 3,000 cycles per minute will act to loosen materials of the surfaces of the footwear causing the materials to dislodge and fall between the openings in the footwear sanitizer grate platform 205 into a debris collection container 230 of one embodiment of the present invention.

Another form of debris removal modules 130 can for example be brushes 224. The bristles of the brushes 224 can be configured around a cylinder and rotated by a motor. In this example the cylindrical brushes 224 while rotating can travel along a tracked guide to cause the bristle to brush against the surfaces of the footwear to scrub loose the debris. The programmable digital cycle timer controller 220 can be set to first activate the vibrating mode and then cycle to dry brushing followed by the spraying of forms of antibacterial treatments 140 of one embodiment of the present invention.

One form of antibacterial treatments 140 can be a liquid antibacterial compound for example chlorine held in an antibacterial compound reservoir 240. In this example the liquid chlorine can be pumped from the antibacterial compound reservoir 240 using a pump sprayer 226. The liquid can be pumped through piping that can be configured with sprayer nozzles 227 washing debris from the surfaces of the sides and soles of the user footwear 200 into the debris collection container 230. The programmable digital cycle timer controller 220 can be set to return the rotating cylindrical brushes 224 back to their starting position thus wet scrubbing the footwear surfaces and sanitizing the bristles at the same time of one embodiment of the present invention. Another form of the antibacterial treatments 140 can be for example one or more ultra violet light source 228 positioned beneath the footwear sanitizer grate platform 205 to provide bacterial killing exposure of the footwear surfaces to bacterial killing ultra violet light. The programmable digital cycle timer controller 220 can be set to regulate for example the exposure time to provide a thorough disinfecting cycle. The footwear sanitizer 120 can be configured to provide debris removal modules 130 that effectively physically remove contaminated materials form the user footwear 200 and disinfect the surfaces of the user footwear 200 using the antibacterial treatments 140 to prevent contamination from entering a sterile environment. The continuation of the processes of the antibacterial door mat 110 continue as shown in FIG. 2B of one embodiment of the present invention.

Bio Detector Platform System:

FIG. 2B shows a block diagram of an overview flow chart of an antibacterial door mat system bio detector platform system of one embodiment of the present invention. FIG. 2B shows the continuation of the processes of the antibacterial door mat 110 from FIG. 2A. Upon completion of the operations of the debris removal modules 130 of FIG. 2A the user steps onto the bio detector platform 150 of the antibacterial door mat 110. This positions the user footwear 200 on the bio detector platform 150 which can be configured with a level standing platform surface using materials for example a clear or translucent acrylic or tempered glass. The programmable digital cycle timer controller 220 can be configured for example with a momentary delayed start of a bio detection cycle triggered by sensors activated by the weight of the user. The bio detection cycle can be configured to begin by turning on one or more bio sensor systems 250 of one embodiment of the present invention.

The bio sensor systems 250 can be configured to include for example one or more infrared array 252. The infrared array 252 can project infrared light onto the surfaces of the soles and lower portions of the user footwear 200. The infrared light energy absorbed by any bacteria or microorganisms present will for example produce a reflective spectrum of colors. Researchers have found that different bacteria and microorganisms reflect a distinguishable color spectrum respectively of one embodiment of the present invention.

The bio detector platform 150 can be configured to include a chromatographic scanner 256 positioned underneath the clear or translucent surface of the bio detector platform 150. This position allows the chromatographic scanner 256 to scan the reflective color spectrum produced by one or more infrared array 252 reflecting off the infrared light projected onto the exposed surfaces of the user footwear 200. The data sensed by the chromatographic scanner 256 is transmitted to a CPU micro processor 260 housed within the bio detector platform 150 of one embodiment of the present invention.

The CPU micro processor 260 is configured with for example digital codes and instructions to search a bio detector database 262 programmed into the CPU micro processor 260. The bio detector database 262 search is to compare any reflective color spectrum patterns obtained from the scan to those within the bio detector database 262 composed of known color spectrum patterns for various bacteria and microorganisms. If a match is found this would indicate the presence of that bacteria or microorganism on the surface footwear of one embodiment of the present invention.

The bio sensor systems 250 can be configured to include for example one or more laser array 254. The laser array 254 can be configured with various frequencies of laser light to project onto the surfaces of the soles and lower portions of the user footwear 200. The laser light energy absorbed by any bacteria or microorganisms present will for example produce a reflective spectrum of colors. The reflective color spectrum will vary depending on the frequency of the laser light projected by the laser array 254. Researchers have found that different bacteria and microorganisms reflect a distinguishable color spectrum respectively from the different laser light frequencies of one embodiment of the present invention.

The bio detector platform 150 using the chromatographic scanner 256 can be configured for example to scan the laser light reflective color spectrum reflected from the surfaces of the soles and lower portions of the user footwear 200. The laser light reflective color spectrum patterns data collected by the chromatographic scanner 256 is compared through a search of the bio detector database 262 programmed into the CPU micro processor 260 containing known laser light reflective color spectrum patterns for various bacteria and microorganisms. If a match is found this would indicate the presence of that bacteria or microorganism on the surface footwear of one embodiment of the present invention.

The results of both exposure scans are used to determine the status of the bio detector clearance 264 thresholds programmed into the CPU micro processor 260. If negative scan search results indicating no presence of contamination are determined then a pass 266 signal is generated and transmitted to a clearance status indicator 270. The clearance status indicator 270 is positioned on the upper surface of the bio detector platform 150 to notify the user of the passing clearance status. If one or more of the can results are positive indicating the presence of contamination are determined then a fail 268 signal is generated and transmitted to a clearance status indicator 270. The clearance status indicator 270 notifies the user that they do not have clearance to enter and can return to the footwear sanitizer 120 of FIG. 1 for additional cleaning cycles of one embodiment of the present invention.

The CPU micro processor 260 can be configured with a digital interface 280 to relay the pass 266 signal to a clearance status indicator 270 on the inside of the sterile area for example behind a locked entry door. The digital interface 280 can be configured as a hard wired connection or a wireless transmitting connection. The bio detector platform 150 can be configured with other types of bio sensor systems 250 for example fluorescent dyes being sprayed on the surfaces of the soles to cause bacteria and microorganisms to produce fluorescence that can be detected using the chromatographic scanner 256. The bio detector platform 150 of the antibacterial door mat 110 provides and effective means to detect biological bacteria and other organisms on the surfaces of the soles and lower portions of footwear prior to entry into a sterile area. The continuation of the processes of the antibacterial door mat system 100 of FIG. 1 continue as shown in FIG. 2C of one embodiment of the present invention.

Bio Detection Clearance Door Entry System:

FIG. 2C shows a block diagram of an overview flow chart of an antibacterial door mat system bio detection clearance door entry system of one embodiment of the present invention. FIG. 2C shows the continuation of the processes of the antibacterial door mat system 100 of FIG. 1 from FIG. 2B. The bio detector clearance 264 results of the antibacterial door mat 110 bio detector platform 150 transmitted through the digital interface 280 can be configured to be received by the bio detection clearance door entry system 170. The bio detection clearance door entry system 170 can be configured with a CPU micro processor 282 located inside the sterile area. The CPU micro processor 282 can be configured to connect to the digital interface 280 by a hard wired connection or a wireless connection. The CPU micro processor 282 can be configured with a monitor to display the bio detector clearance 264 clearance status indicator 270 signals of pass 266 or fail 268. The displayed clearance status indicator 270 signals can for example be used by personnel inside the sterile area such as a security guard to open the door and allow entry of the user of one embodiment of the present invention.

The CPU micro processor 282 can be configured to automatically transmit an unlock command 292 to a digitally controlled locking mechanism 290 to open the door and allow entry of the user. The CPU micro processor 282 can be configured to allow personnel inside the sterile area such as a security guard to activate a manual override 294 of the digitally controlled locking mechanism 290 to allow entry in cases of a false reading or system failure. The entry control provided by the bio detection clearance door entry system 170 will reduce or prevent footwear borne contamination of bacteria and microorganisms into areas of sterile environments of one embodiment of the present invention.

Figure 3:
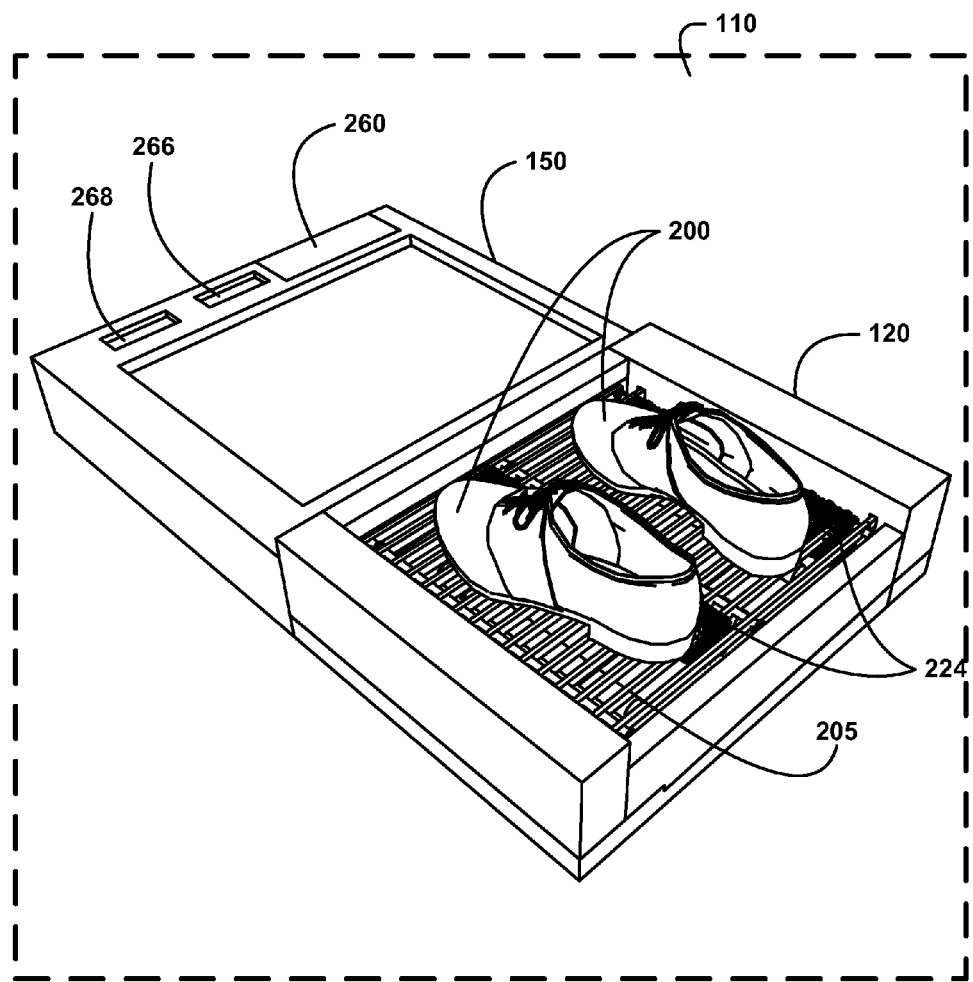
FIG. 3 shows for illustrative purposes only an example of an antibacterial door mat of one embodiment of the present invention.

Antibacterial Door Mat:

FIG. 3 shows for illustrative purposes only an example of an antibacterial door mat of one embodiment of the present invention.

FIG. 3 shows one example of the antibacterial door mat 110 of the antibacterial door mat system 100 of FIG. 1. The antibacterial door mat 110 can be configured for example of a physical size covering the approximate floor area size of a standard door mat. The footwear sanitizer 120 can be configured to provide ample standing space for the user footwear 200. The user will stand on the footwear sanitizer grate platform 205 which can be configured to provide sufficient structural support to bear the weight of the user. The brushes 224 can be configured to allow the bristles to fit in the openings of the footwear sanitizer grate platform 205 of one embodiment of the present invention.

The bio detector platform 150 can also be configured to provide ample standing space for the user footwear 200. The clear or translucent surface of the bio detector platform 150 can be configured of materials and supports to provide sufficient structural support to bear the weight of the user. The CPU micro processor 260 is attached within the housing of the bio detector platform 150. The upper surface of the bio detector platform 150 and be configured to have attached and connected both the pass 266 and fail 268 clearance status indicator 270 of FIG. 2B signal displays. The antibacterial door mat 110 can be configured as a compact conveniently sized and effective means to reduce and prevent bacterial and microorganism contamination of sterile environment areas of one embodiment of the present invention.

The foregoing has described the principles, embodiments and modes of operation of the present invention. However, the invention should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. A footwear sanitizing device comprising:
   a housing,
   a grate platform associated with the housing,
   a debris removal module disposed in the housing,
   a debris collection container disposed in the housing,
   a component for providing antibacterial treatment disposed in the housing,
   a bio detector platform associated with the housing, the platform comprising a surface for standing, and
   at least one bio sensor system disposed in the housing for detecting bacteria and other biological microorganisms on the footwear.

2. The device of claim 1 wherein the at least one bio sensor system includes at least one of the following:

an infrared array for projecting infrared light onto the footwear, and a laser array for projecting laser light onto the footwear.

3. The device of claim 2 wherein the bio sensor system includes a chromatographic scanner for scanning for reflective color spectrum values produced by the infrared array or the laser array, and a CPU micro processor for receiving data from the chromatographic scanner and performing a digital search comparison with a bio detector database programmed into the CPU micro processor.

4. The device of claim 3 wherein the bio sensor system further comprises a bio detector clearance algorithm for determining the status results of the digital search comparison in the bio detector database, wherein the bio detector clearance algorithm generates a pass or fail signal for transmitting to a clearance status indicator.

5. The device of claim 4 wherein the platform is transparent.

6. The device of claim 5 wherein the bio sensor system includes one or more of optical, staining and gas analysis sensing for detecting bacteria and microorganisms.

* * * * *